US010905391B2

(12) United States Patent
Chandelier et al.

(10) Patent No.: US 10,905,391 B2
(45) Date of Patent: Feb. 2, 2021

(54) METHOD AND SYSTEM FOR DISPLAYING TO A USER A TRANSITION BETWEEN A FIRST RENDERED PROJECTION AND A SECOND RENDERED PROJECTION

(71) Applicant: Imagia Healthcare Inc., Montréal (CA)

(72) Inventors: Florent André Robert Chandelier, Granby (CA); Thomas Bernard Pascal Vincent, Brossard (CA)

(73) Assignee: Imagia Healthcare Inc., Montréal (CA)

( * ) Notice: Subject to any disclaimer, the term of this patent is extended or adjusted under 35 U.S.C. 154(b) by 0 days.

(21) Appl. No.: 14/646,548

(22) PCT Filed: Nov. 22, 2013

(86) PCT No.: PCT/CA2013/000982
§ 371 (c)(1),
(2) Date: May 21, 2015

(87) PCT Pub. No.: WO2014/078944
PCT Pub. Date: May 30, 2014

(65) Prior Publication Data
US 2015/0335303 A1 Nov. 26, 2015

Related U.S. Application Data

(60) Provisional application No. 61/729,472, filed on Nov. 23, 2012.

(51) Int. Cl.
*G06T 15/10* (2011.01)
*A61B 6/00* (2006.01)
(Continued)

(52) U.S. Cl.
CPC .......... *A61B 6/466* (2013.01); *A61B 5/055* (2013.01); *A61B 6/467* (2013.01); *A61B 6/5223* (2013.01);
(Continued)

(58) Field of Classification Search
None
See application file for complete search history.

(56) References Cited

U.S. PATENT DOCUMENTS 5,474,078 A 12/1995 Hutson
6,633,686 B1 10/2003 Bakircioglu et al.
(Continued)

FOREIGN PATENT DOCUMENTS

CN 1723852 A 1/2006
JP 11-299782 11/1999
(Continued)

OTHER PUBLICATIONS

SG 11201503711Y, Search Report, Issued by Intellectual Property Office of Singapore, dated Mar. 9, 2016.
(Continued)

*Primary Examiner* — Anh-Tuan V Nguyen
(74) *Attorney, Agent, or Firm* — Wiggin and Dana LLP; Gregory S. Rosenblatt; Thomas M. Landman

(57) ABSTRACT

A method and an apparatus are disclosed for displaying to a user a transition between a first rendered projection of a first image data and a final rendered projection of a second image data, the method comprising obtaining said first image data and said second image data, each generated by a corresponding 3D scanning device scanning a structure; displaying a first view corresponding to a first rendered projection of said first image data in a given window; obtaining an input from the user, said input being indicative of said final rendered projection of a portion of said second image data and displaying in sequence a plurality of views in the given window, each view corresponding to a different rendered projection of at least one of the first image data and the second image data, wherein the plurality of rendered projections are defined so as to perform a transition between the first rendered projection and the final rendered projection, further wherein the transition enables a sequential display of a continuity of information of said structure from said first image data to said portion of said second image data, further wherein at least one of said first rendered projection and said final rendered projection are defined according to a different (Continued)

spatial arrangement and said first image data and said second image data are generated by different 3D scanning devices.

21 Claims, 11 Drawing Sheets

(51) Int. Cl.
  *A61B 8/00*     (2006.01)
  *G06T 19/00*    (2011.01)
  *G06T 13/80*    (2011.01)
  *A61B 5/055*    (2006.01)
  *A61B 6/03*     (2006.01)
  *A61B 8/08*     (2006.01)
  *A61B 6/02*     (2006.01)

(52) U.S. Cl.
  CPC ............ *A61B 6/5247* (2013.01); *A61B 8/466* (2013.01); *A61B 8/467* (2013.01); *G06T 13/80* (2013.01); *G06T 19/003* (2013.01); *A61B 6/025* (2013.01); *A61B 6/032* (2013.01); *A61B 6/037* (2013.01); *A61B 6/463* (2013.01); *A61B 8/463* (2013.01); *A61B 8/483* (2013.01); *A61B 8/523* (2013.01); *A61B 2576/00* (2013.01); *G06T 2210/41* (2013.01); *G06T 2219/028* (2013.01)

(56) References Cited

U.S. PATENT DOCUMENTS

| | | | | |
|---|---|---|---|---|
| 7,558,611 | B2* | 7/2009 | Arnold | G06T 7/0012 128/922 |
| 7,890,887 | B1* | 2/2011 | Linardos | G01R 33/543 709/236 |
| 7,894,663 | B2 | 2/2011 | Berg et al. | |
| 8,115,760 | B2* | 2/2012 | Rust | G06T 19/00 345/419 |
| 8,334,867 | B1* | 12/2012 | Davidson | G06F 3/04815 345/419 |
| 8,860,717 | B1* | 10/2014 | Zeiger | G06T 13/00 345/419 |
| 9,235,575 | B1* | 1/2016 | Xiao | G06F 16/4393 |
| 2004/0047497 | A1 | 3/2004 | Daw et al. | |
| 2004/0056857 | A1* | 3/2004 | Zhang | G06K 9/00268 345/419 |
| 2005/0041842 | A1* | 2/2005 | Frakes | G06K 9/3216 382/128 |
| 2005/0110788 | A1* | 5/2005 | Turner | G06F 19/321 345/419 |
| 2005/0134610 | A1* | 6/2005 | Doyle | G06T 3/0018 345/647 |
| 2006/0034513 | A1 | 2/2006 | Cai et al. | |
| 2006/0036150 | A1 | 2/2006 | Lutz et al. | |
| 2006/0079746 | A1* | 4/2006 | Perret | A61B 5/02007 600/407 |
| 2006/0132482 | A1* | 6/2006 | Oh | G06T 13/80 345/419 |
| 2007/0016853 | A1* | 1/2007 | Abagyan | G06T 19/00 715/251 |
| 2008/0008366 | A1* | 1/2008 | Desh | G06T 19/00 382/128 |
| 2008/0118132 | A1 | 5/2008 | Ubelhart et al. | |
| 2008/0242968 | A1 | 10/2008 | Claus et al. | |
| 2008/0246768 | A1* | 10/2008 | Murray | G06T 15/08 345/427 |
| 2009/0003665 | A1 | 1/2009 | Berg et al. | |
| 2009/0304250 | A1* | 12/2009 | McDermott | A61B 8/08 382/131 |
| 2009/0322764 | A1* | 12/2009 | Saini | G06T 1/20 345/501 |
| 2010/0037182 | A1 | 2/2010 | Biglieri et al. | |
| 2010/0097378 | A1* | 4/2010 | Barth | A61B 6/466 345/427 |
| 2010/0171759 | A1* | 7/2010 | Nickolov | G06T 3/40 345/634 |
| 2010/0208957 | A1 | 8/2010 | Chen et al. | |
| 2010/0254584 | A1* | 10/2010 | Gulsun | A61B 5/055 382/131 |
| 2010/0283781 | A1* | 11/2010 | Kriveshko | G06T 17/00 345/419 |
| 2010/0333017 | A1* | 12/2010 | Ortiz | G06F 3/0486 715/800 |
| 2011/0018864 | A1* | 1/2011 | Ishibashi | G06F 3/011 345/419 |
| 2011/0090215 | A1* | 4/2011 | Ohta | H04N 13/275 345/419 |
| 2011/0176720 | A1* | 7/2011 | Van Osten | G06T 13/80 382/154 |
| 2011/0178389 | A1 | 7/2011 | Kumar et al. | |
| 2011/0222750 | A1* | 9/2011 | Liao | A61B 6/4441 382/131 |
| 2011/0248987 | A1* | 10/2011 | Mitchell | G06T 15/20 345/419 |
| 2011/0274330 | A1 | 11/2011 | Mori et al. | |
| 2012/0011457 | A1* | 1/2012 | Habets | G06T 15/20 715/769 |
| 2012/0050278 | A1* | 3/2012 | Iizuka | G06T 7/0012 345/419 |
| 2012/0081362 | A1* | 4/2012 | Kiraly | G06T 19/00 345/419 |
| 2012/0087561 | A1* | 4/2012 | Guetter | G06T 7/174 382/131 |
| 2012/0101370 | A1 | 4/2012 | Razzaque et al. | |
| 2012/0131498 | A1* | 5/2012 | Gross | G06F 17/30274 715/788 |
| 2012/0139906 | A1* | 6/2012 | Zhang | H04N 13/156 345/419 |
| 2012/0154446 | A1* | 6/2012 | Adams | G06T 3/0081 345/661 |
| 2012/0259224 | A1* | 10/2012 | Wu | A61B 8/485 600/443 |
| 2012/0265050 | A1 | 10/2012 | Wang | |
| 2013/0113816 | A1* | 5/2013 | Sudarsky | G06T 11/206 345/589 |
| 2013/0129177 | A1* | 5/2013 | Meinel | G06K 9/34 382/131 |
| 2013/0187903 | A1* | 7/2013 | Papageorgiou | G06T 19/00 345/419 |
| 2013/0328874 | A1* | 12/2013 | Smith-Casem | G06T 15/30 345/424 |
| 2014/0047380 | A1* | 2/2014 | Mak | G06F 3/04883 715/800 |
| 2014/0143716 | A1* | 5/2014 | Buelow | G06T 7/0079 715/788 |
| 2015/0161813 | A1* | 6/2015 | Hernandez Esteban | G06T 1/60 345/427 |

FOREIGN PATENT DOCUMENTS

| | | |
|---|---|---|
| JP | 2009-291596 | 12/2009 |
| JP | 2012231235 | 11/2012 |
| WO | WO 2006121779 | 11/2006 |
| WO | WO 2006134565 | 12/2006 |
| WO | 2009/070160 A1 | 6/2009 |
| WO | 2011/117788 A1 | 9/2011 |
| WO | WO 2012155136 | 11/2012 |
| WO | 2013010261 A2 | 1/2013 |

OTHER PUBLICATIONS

Shuo Jin, et al., "Registration of PET and CT Images Based on Multiresolution Gradient of Mutual Information Demons Algorithm for Positioning Esophageal Cancer Patients," published in Journal of Applied Clinical Medical Physics, vol. 14, No. 1, pp. 50-61, Jan. 2013.

(56) References Cited

OTHER PUBLICATIONS

Kniss, Joe et al., "Multi-Dimensional Transfer Functions for Interactive vol. Rendering," published in IEEE Transaction on Visualization and Computer Graphics, vol. 8(3), pp. 270-285, Jul. 2002.
PCT/CA2013/000982, International Search Report, dated Mar. 2014.
Official Decision of Refusal in related Japanese Application No. 2015-543221, dated Feb. 20, 2018, 11 pages.
Communication from EPO in related application 13856130.3, dated Jan. 22, 2018, 8 pages.
Notification from Israel Patent Office in related application 238682, dated Dec. 17, 2017, 7 pages.
Communication from Canadian Intellectual Property Office in related application No. 2,892,326, dated Jan. 4, 2019, 10 pages.

* cited by examiner

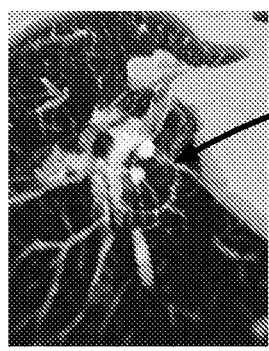  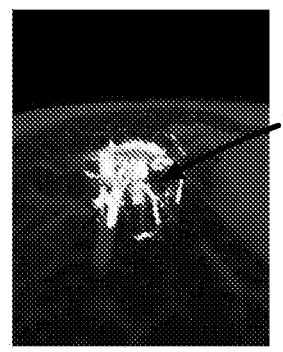
FIG. 29    FIG. 30    FIG. 33
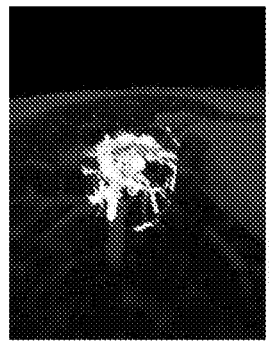 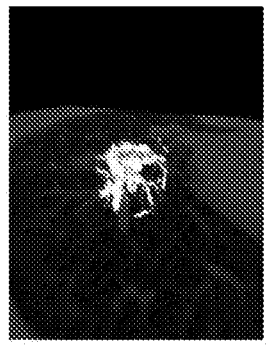 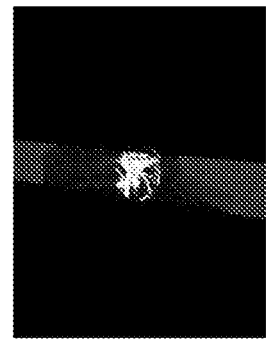
FIG. 34    FIG. 35    FIG. 36
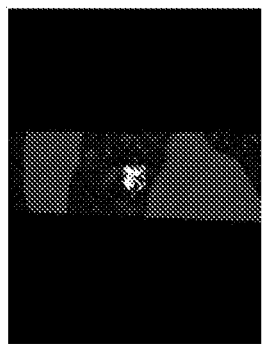 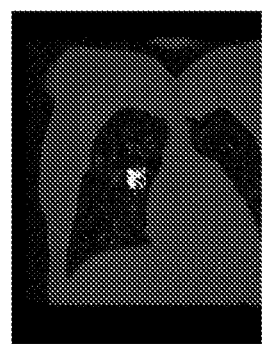
FIG. 37    FIG. 38 ved herein
METHOD AND SYSTEM FOR DISPLAYING TO A USER A TRANSITION BETWEEN A FIRST RENDERED PROJECTION AND A SECOND RENDERED PROJECTION

CROSS-REFERENCE TO RELATED APPLICATION

The present patent application is a national stage filing of International Application Number PCT/CA2013/000982, filed Nov. 22, 2013, which claims the benefit of U.S. Provisional Patent Application No. 61/729,472, filed on Nov. 23, 2012, the contents of which is incorporated herein by reference.

FIELD

The invention relates to imaging. More precisely, the invention pertains to a method and a system for displaying to a user a transition between a first rendered projection and a second rendered projection.

BACKGROUND

As visualization technologies progress, medical imaging solutions have been providing healthcare professionals with more advanced visual support for the purpose of enhancing diagnosis. Scanning image acquisition technologies have evolved, leading to an ever increasing amount of data generated for a given exam.

Medical imaging solutions have implemented various graphical user interfaces (GUI) to support healthcare professionals in the reviewing of larger and larger image data, including any data rendered in the form of image or blended into images, to support the examination of imaging data. The purpose of those solutions is to provide correlations and combined analysis to enhance final diagnosis.

One form of data examination is the analysis of 2D and 3D information in forms of thin slices, that is raw information provided by a scanner, thick slices, that is information of multiple thin slices projected onto a given plane, and 3D reconstruction of any of the above.

Graphical user interfaces have been extended by multiple viewports as placeholders for multiple views, rendered projection of image data, albeit 2D thin slice, 2D thick slice, and 3D reconstruction.

Some solutions provided to support healthcare professionals in correlating information throughout these GUI viewports have focused on overlaying nonclinical information onto each of the viewports for a human to cognitively correlate given region of interest. Unfortunately many limitations still remain in the prior art.

For instance, a first limitation of current prior-art methods is that the introduction of nonclinical information onto clinical information displayed to the healthcare professionals eventually obstructs clinically relevant aspects of the rendered information.

A second limitation of current prior-art methods is that there is a great amount of non-diagnostic oriented cognitive process required by healthcare professionals to perform such anatomical correlation using such overlays.

A third limitation of current prior-art methods is that they use multiple viewports within a given GUI, while a user can interact and focus solely on a unique view at a given time. As such, if a different rendered projection image of image data is required for examination and diagnosis, the user has to change his visual focus to a different view location, thus losing visual coherence for a moment. In addition, there is a waste of visualization space simply for the sake of providing healthcare professionals with the means to examine medical imaging information in different formatting.

A fourth limitation of current prior art methods is that, as a result of the combination of the previous limitations, when changing visualization paradigm, albeit between 2D thin slice anatomical planes, such as from axial to coronal projections, healthcare professionals are presented with "out-of-the-blue" reformatting of information, without coherent relation. This requires a great deal of cognitive efforts for the operator to correlate previous formatting to current formatting.

A fifth limitation of current prior-art methods appears when a 3D reconstruction is involved. Most of the time, it is difficult, if not impossible, to predict the kind of structures that will arise during a 3D reconstruction simply by looking at a given plane, even if presented with multiple visual representations of it. There is thus a disconnection between 3D representation and 2D representation, that again requires cognitive efforts in order to correlate both pieces of information.

Another limitation, yet fundamentally different, is the fact that in the course of examination, an operator is led to different image manipulations (such as zooming in and out, and panning), mixing 2D and 3D information, but cannot go back to where the process started in terms of location and state. This is a great limitation which forces the operator to always question if he/she looked at the complete image data.

FIG. 1 shows, for instance, 3 typical anatomical planes, sagittal, axial and coronal, with their 3D superposition. As shown in FIG. 1, the point of interest is presented at the intersection of the lines in every image. The intersection at the center of the 3D representation is totally obscured and thus clinically irrelevant. It will be appreciated that in this embodiment an operator will have to look at each of the anatomical planes sequentially in order to obtain desired information.

In FIG. 2, there is illustrated a representation of the examination of a dental implant. In order to obtain clinically relevant information on depth structure, four different views, including a cross-section view were created. A diagnosis can be made only by examining the images in sequence.

In FIG. 3, the region of interest is the intersection of the colored lines. The skilled addressee will appreciate that for complex anatomical structures, such visually decorrelated information is hard to process, and it requires experienced cognitive processes.

In FIG. 5, a choice of graphics users interface was made to provide each of the relevant anatomical planes along with their reconstruction. Blue arrows are overlaid on the 2D anatomical planes corresponding to the center of the 3D camera in order to help the operator to stay focused. Considering the fact that each image is synchronized to the 3D, moving one step in the 3D will trigger the rendering of new 2D images, all images moving at once. This is clearly not convenient considering the human capacity of visual analysis.

In FIG. 6, another graphical user interface is shown for a similar application. In this graphical user interface, dynamics lines are overlaid on the 2D images to correlate with the 3D reconstruction view.

In FIG. 7, another type of information superposition is obtained for the correlation of 2 3D information. It can be clearly seen that such color and overlays alter the ability to diagnose a given region of interest and introduce nonclinical information on the final visual information provided to the operator.

FIG. 8 shows another example in which the axial anatomical plane is represented by a red thick line on the 3D view, introducing nonclinical information on the 3D view for the sole purpose of supporting the operator when correlating the information.

FIG. 9 shows another prior art graphical user interface for functional information.

FIG. 10 shows another example of a prior-art graphical user interface for displaying data from an ultrasound device which also shows some of the limitations disclosed above.

There is therefore a need for a method that will overcome at least one of the above-identified drawbacks.

Features of the invention will be apparent from review of the disclosure, drawings and description of the invention below.

BRIEF SUMMARY

According to one aspect, there is disclosed a method for displaying to a user a transition between a first rendered projection of a first image data and a final rendered projection of a second image data, the method comprising obtaining said first image data and said second image data, each generated by a corresponding 3D scanning device scanning a structure; displaying a first view corresponding to a first rendered projection of said first image data in a given window obtaining an input from the user, said input being indicative of said final rendered projection of a portion of said second image data and displaying in sequence a plurality of views in the given window, each view corresponding to a different rendered projection of at least one of the first image data and the second image data, wherein the plurality of rendered projections are defined so as to perform a transition between the first rendered projection and the portion of the final rendered projection, further wherein the transition enables a sequential display of a continuity of information of said structure from said first image data to said second image data, further wherein at least one of said first rendered projection and said final rendered projection are defined according to a different spatial arrangement and said first image data and said second image data are generated by different 3D scanning devices.

According to another aspect, there is a system for displaying to a user a transition between a first rendered projection of a first image data and a final rendered projection of a second image data, the system comprising a display device; a central processing unit; a memory comprising a database for storing the first image data and the second image data and an application for displaying to a user a transition between a first rendered projection of a first image data and a final rendered projection of a second image data, the application comprising instructions for obtaining said first image data and said second image data, each generated by a corresponding 3D scanning device scanning a structure; instructions for displaying a first view corresponding to a first rendered projection of said first image data in a given window; instructions for obtaining an input from the user, said input being indicative of said final rendered projection of a portion of said second image data; instructions for displaying in sequence a plurality of views in the given window, each view corresponding to a different rendered projection of at least one of the first image data and the second image data, wherein the plurality of rendered projections are defined so as to perform a transition between the first rendered projection and the final rendered projection, further wherein the transition enables a sequential display of a continuity of information of said structure from said first image data to said portion of said second image data, further wherein at least one of said first rendered projection and said final rendered projection are defined according to a different spatial arrangement and said first image data and said second image data are generated by different 3D scanning devices.

According to another aspect, there is disclosed a non-transitory computer-readable storage medium for storing computer-executable instructions which when executed cause a computing device to perform a method for displaying to a user a transition between a first rendered projection of a first image data and a final rendered projection of a second image data, the method comprising obtaining said first image data and said second image data, each generated by a corresponding 3D scanning device scanning a structure; displaying a first view corresponding to a first rendered projection of said first image data in a given window; obtaining an input from the user, said input being indicative of said final rendered projection of a portion of said second image data; displaying in sequence a plurality of views in the given window, each view corresponding to a different rendered projection of at least one of the first image data and the second image data, wherein the plurality of rendered projections are defined so as to perform a transition between the first rendered projection and the final rendered projection, further wherein the transition enables a sequential display of a continuity of information of said structure from said first image data to said portion of said second image data, further wherein at least one of said first rendered projection and said final rendered projection are defined according to a different spatial arrangement and said first image data and said second image data are generated by different 3D scanning devices.

In accordance with an embodiment, the 3D scanning device is selected from a group consisting of at least one of a computerized tomography (CT) scan device, a tomosynthesis device, a magnetic resonance imaging (MRI) device, a positron emission tomography (PET) device and an ultrasound device.

In accordance with an embodiment, the first rendered projection of the first image data is selected from a group consisting of 2D thin slice, 2D thick slice, 2D maximum intensity projection, 3D ray-tracing, 3D surface rendering, 3D perspective projection, 3D endoscopic projection and world projection.

In accordance with an embodiment, the final rendered projection is selected from a group consisting of 2D thin slice, 2D thick slice, 2D maximum intensity projection, 3D ray-tracing, 3D surface rendering, 3D perspective projection, 3D endoscopic projection and world projection.

In accordance with an embodiment, the first image data is generated by a first 3D scanning device scanning the structure and said second image data is generated by a second 3D scanning device scanning the structure.

In accordance with an embodiment, the first image data and the second image data are generated by a single 3D scanning device scanning the structure.

In accordance with an embodiment, the first image data and the second image data are the same.

In accordance with an embodiment, the obtaining of an input from the user comprises obtaining the input from at least one of a keyboard and a mouse.

In accordance with an embodiment, the displaying of the first view corresponding to a first rendered projection of said first image data in a given window is performed on a touchscreen display and the obtaining of an input from the user comprises detecting a finger gesture on said touchscreen display.

In accordance with an embodiment, the obtaining of the first image data and the second image data comprises receiving the first image data and the second image data from a 3D scanning device scanning the structure.

In accordance with an embodiment, the obtaining of the first image data and the second image data comprises retrieving from a memory the first image data and the second image data.

In accordance with an embodiment, the obtaining of an input from the user comprises obtaining an indication of the final rendered projection of a portion of the second image data and an indication of a zoom to perform on a region of interest in a given view and the method further comprises generating a plurality of zoomed views in the given view, further wherein the plurality of views in the given windows comprises the generated plurality of zoomed views.

In accordance with an embodiment, the system further comprises a communication port operatively connected to the central processing unit, the connection port for operatively connecting the system to a remote 3D scanning device scanning the structure.

In accordance with an embodiment, the communication port is operatively connected to the remote 3D scanning device scanning the structure via a data network.

In accordance with an embodiment, the data network is selected from a group consisting of a local area network (LAN), a metropolitan area network (MAN) and a wide area network (WAN).

In accordance with an embodiment, the data network comprises the Internet.

In accordance with an embodiment, the display device is a touchscreen display and at least one part of the input of the user is obtained from the touchscreen display.

In accordance with an embodiment, at least one of the plurality of views further comprises visual information displayed which is associated to at least one of an associated rendered projection and the input from the user.

In accordance with an embodiment, the input from the user further comprises location property data in the first image data and the location property data is used for determining rendering parameters associated with rendered projection for subsequent views.

In accordance with an embodiment, the input from the user comprises information associated with a segmentation to perform and the displaying in sequence of a plurality of views in the given window comprises performing a segmentation prior displaying at least one of the plurality of views.

BRIEF DESCRIPTION OF THE DRAWINGS

In order that the invention may be readily understood, embodiments of the invention are illustrated by way of example in the accompanying drawings.

FIG. 29 is a screenshot which shows a view of the sequence of a plurality of views that comes chronologically after the view shown in FIG. 28.

FIG. 30 is a screenshot which shows a view of a plurality of views that comes chronologically after the view shown in FIG. 29.

FIG. 33 is a screenshot which shows a desired final 3D rendering projection image.

FIG. 34 is a screenshot which shows a view similar to the view illustrated at FIG. 33.

FIG. 35 is a screenshot which shows a view of the sequence of a plurality of views that comes chronologically after the view shown in FIG. 34.

FIG. 36 is a screenshot which shows one of the views of the sequence of a plurality of views that comes chronologically after the view shown in FIG. 35.

FIG. 37 is a screenshot which shows one of the views of the sequence of a plurality of views that comes chronologically after the view shown in FIG. 36.

FIG. 38 is a screenshot which shows a final rendered projection image of the portion of image data with respect to a 2D thick coronal rendered projection image of the image data.

Figure 1:
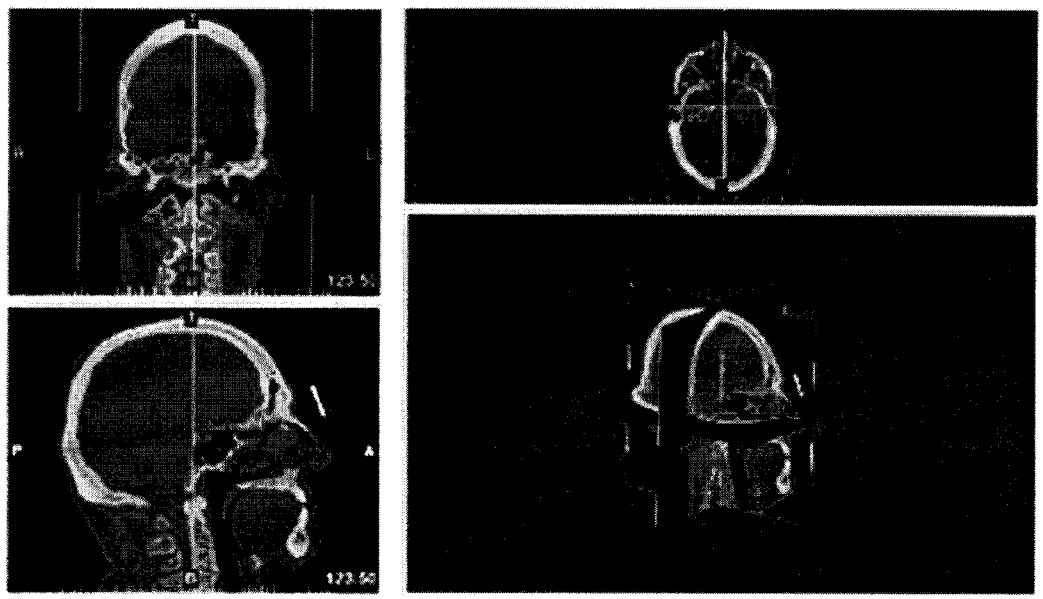
FIG. 1 is a screenshot which shows a first embodiment of a prior-art user interface.
Figure 2:
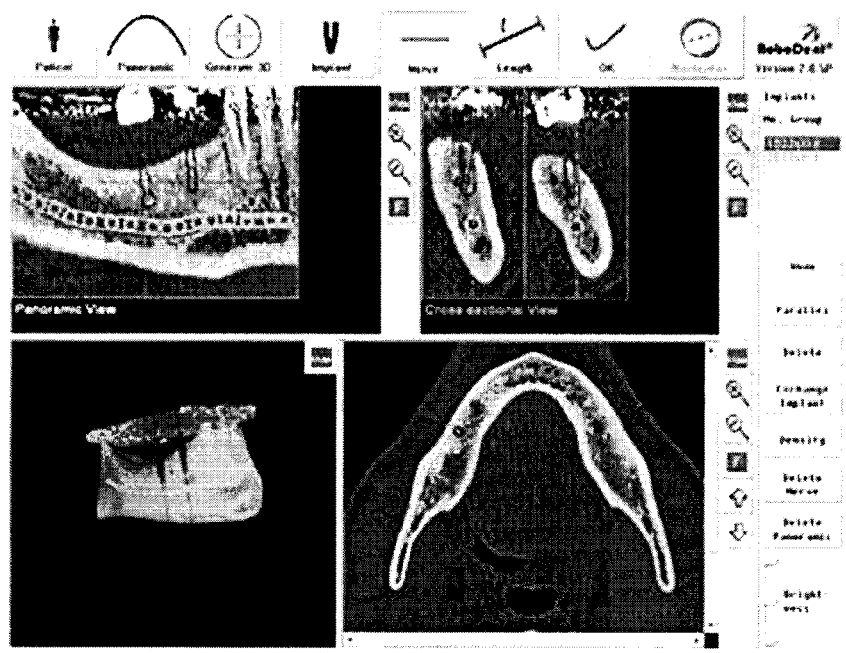
FIG. 2 is a screenshot which shows a second embodiment of a prior-art user interface.
Figure 3:
FIG. 3 is a screenshot which shows a third embodiment of a prior-art user interface.
Figure 4:
FIG. 4 is a screenshot which shows a fourth embodiment of a prior-art user interface.
Figure 5:
FIG. 5 is a screenshot which shows a fifth embodiment of a prior-art user interface.
Figure 6:
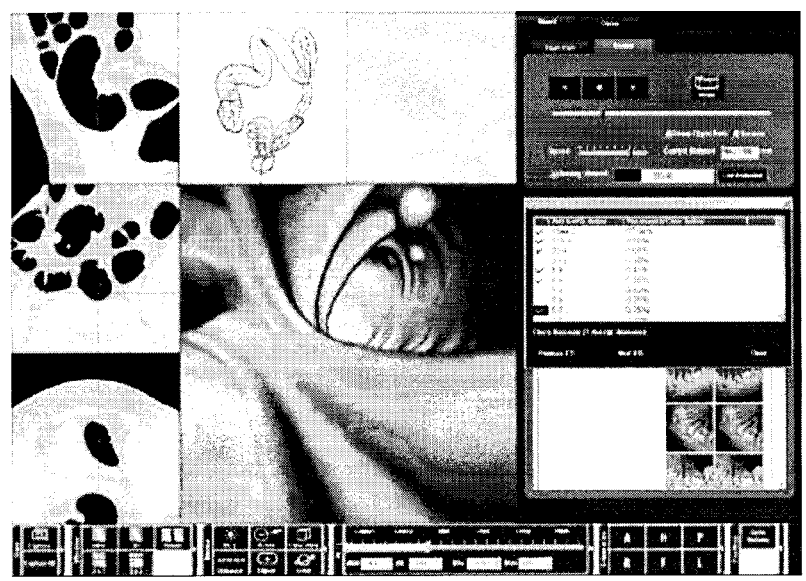
FIG. 6 is a screenshot which shows a sixth embodiment of a prior-art user interface.
Figure 7:
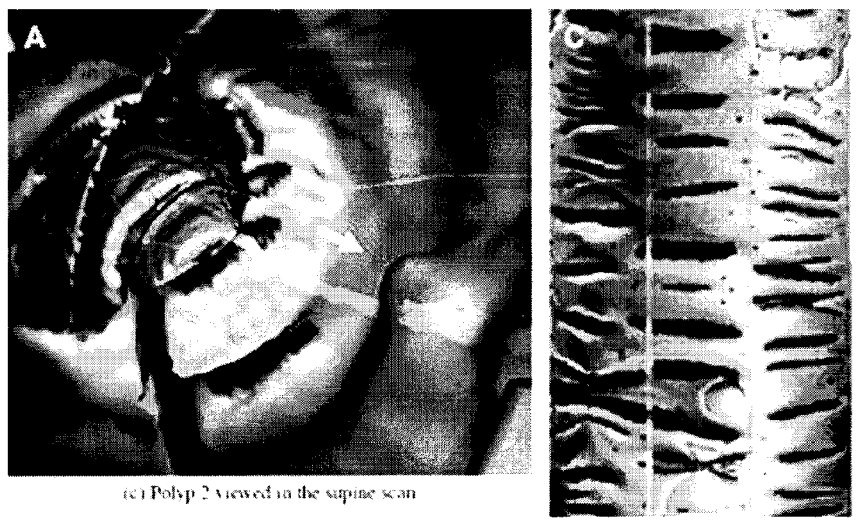
FIG. 7 is a screenshot which shows a seventh embodiment of a prior-art user interface.
Figure 8:
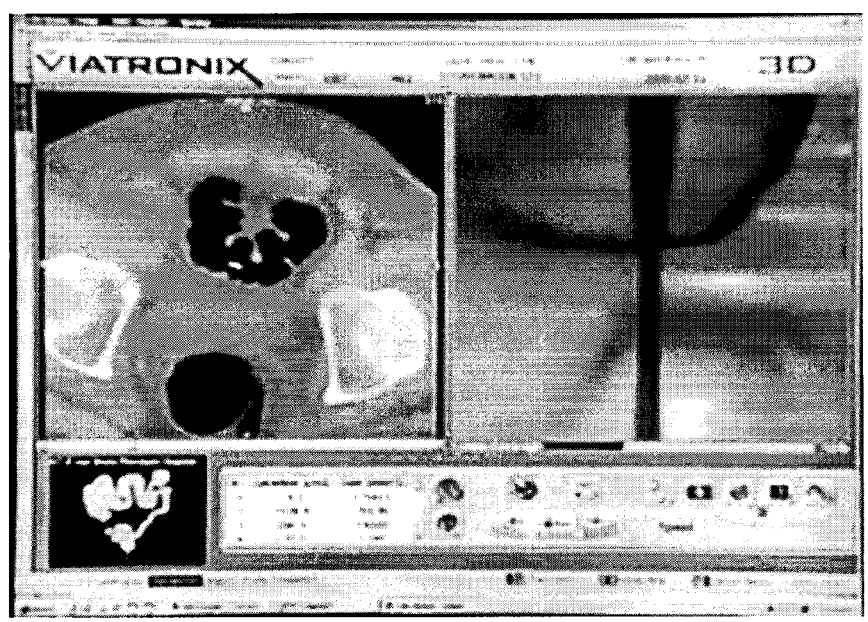
FIG. 8 is a screenshot which shows an eighth embodiment of a prior-art user interface.
Figure 9:
FIG. 9 is a screenshot which shows a ninth embodiment of a prior-art user interface.
Figure 10:
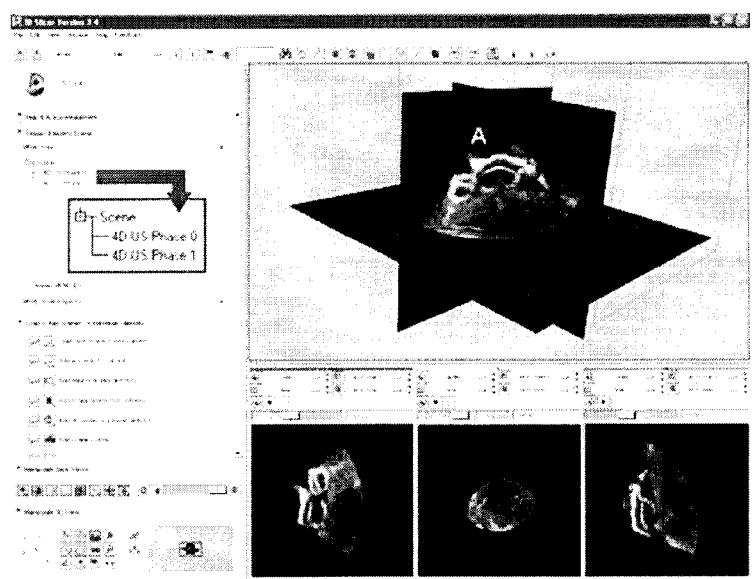
FIG. 10 is a screenshot which shows a tenth embodiment of a prior-art user interface.

Further details of the invention and its advantages will be apparent from the detailed description included below.

DETAILED DESCRIPTION

In the following description of the embodiments, references to the accompanying drawings are by way of illustration of an example by which the invention may be practiced.

Terms

The terms "invention" and the like mean "the one or more inventions disclosed in this application," unless expressly specified otherwise.

The terms "an aspect," "an embodiment," "embodiment," "embodiments," "the embodiment," "the embodiments," "one or more embodiments," "some embodiments," "certain embodiments," "one embodiment," "another embodiment" and the like mean "one or more (but not all) embodiments of the disclosed invention(s)," unless expressly specified otherwise.

A reference to "another embodiment" or "another aspect" in describing an embodiment does not imply that the referenced embodiment is mutually exclusive with another embodiment (e.g., an embodiment described before the referenced embodiment), unless expressly specified otherwise.

The terms "including," "comprising" and variations thereof mean "including but not limited to," unless expressly specified otherwise.

The terms "a," "an" and "the" mean "one or more," unless expressly specified otherwise.

The term "plurality" means "two or more," unless expressly specified otherwise.

The term "herein" means "in the present application, including anything which may be incorporated by reference," unless expressly specified otherwise.

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The terms "e.g." and like terms mean "for example," and thus do not limit the term or phrase they explains. For example, in a sentence "the computer sends data (e.g., instructions, a data structure) over the Internet," the term "e.g." explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "i.e." and like terms mean "that is," and thus limit the term or phrase they explain. For example, in the sentence "the computer sends data (i.e., instructions) over the Internet," the term "i.e." explains that "instructions" are the "data" that the computer sends over the Internet.

The term "image data" and like terms mean unitary image elements constituting image data, e.g., pixels and voxels, and any "materia prima" constituting the unitary digital element of image data, related to information acquired by scanner technologies (CT, MRI, x-rays, ultrasound).

The term "structure" and like terms mean a region of interest constituted of at least part of image data that, when rendered on screen, visually depicts coherent information for the operator amongst which anatomical organs, tissues, cancers.

The term "projection" and like terms mean a mathematical process involved in rendering at least part of image data at a given viewpoint from a desired visual and dimensional perspectives, e.g., 3D surface rendering, 3D volume rendering, 2D Slab-rendering, 2D axial slice rendering, 2D sagittal rendering, 2D coronal rendering, 2D oblique rendering and 2D multi-planar reconstruction.

The terms "user," "operator" and the like, mean a human interacting with the system for displaying to a user a transition between a first rendered projection and a second rendered projection. It will be appreciated that the user has appropriate skills for interacting with the system. In the embodiment where the structure is a part of a human body, the user may be a radiologist.

Neither the Title nor the Abstract is to be taken as limiting in any way the scope of the disclosed invention(s). The title of the present application and headings of sections provided in the present application are for convenience only, and are not to be taken as limiting the disclosure in any way.

Numerous embodiments are described in the present application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural and logical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

It will be appreciated that the invention can be implemented in numerous ways, including as a method, a system, a computer-readable medium such as a non-transitory computer-readable storage medium. In this specification, these implementations, or any other form that the invention may take, may be referred to as systems or techniques. A component such as a processor or a memory described as being configured to perform a task includes both a general component that is temporarily configured to perform the task at a given time or a specific component that is manufactured to perform the task.

With all this in mind, the present invention is directed to a method, system, and computer program product for displaying to a user a transition between a first rendered projection of a first image data and a final rendered projection of a second image data.

Figure 11:
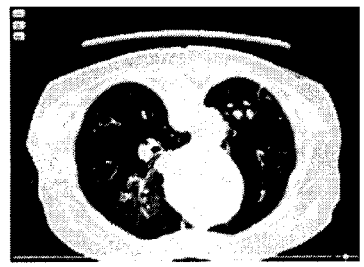
FIG. 11 is a screenshot which shows an initial 2D thick axial projection image.

Now referring to FIG. 11, there is shown an initial 2D thick axial projection image (maximum intensity projection of 6 raw 2D thin axial projections images) obtained at a given slice of image data representing the lung (being the structure taken as a region of interest by the operator), and presenting a nodule within a marked region 100.

Figure 12:
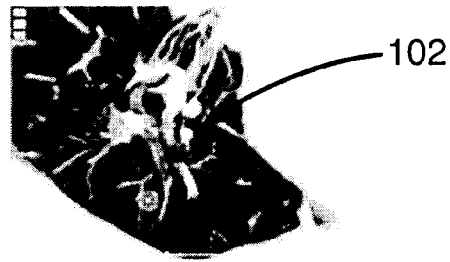
FIG. 12 is a screenshot which shows a zoomed region of interest corresponding to a marked region in FIG. 11.

Referring now to FIG. 12, there is shown a zoomed region of interest corresponding to the marked region 100 shown in FIG. 11 in the 2D thick axial projection. A nodule 102 can be seen (being a further structure taken as a subsequent region of interest by the operator).

It will be appreciated that at some point the user, also referred to as a radiologist or operator, may decide to perform a click on the user interface to toggle the anatomical orientation of the projection, e.g., from an axial projection to a coronal projection.

Figure 13:
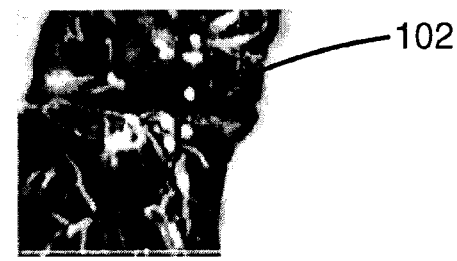
FIG. 13 is a screenshot which shows a final 2D thick coronal projection image.

As shown in FIG. 13, a final 2D thick coronal projection image (equivalent thickness) is obtained by re-slicing the image data at the location of the nodule 102 to render the accumulation of image data element intensities along such thickness.

It will be appreciated that right before the operator performs the click, anatomical orientation was axial, but right after the anatomical orientation becomes coronal. This change of orientation is thus sudden and visually disruptive.

Due to this sudden anatomical orientation modification and although the nodule 102 remains at the center of the final rendered projection image, many visually similar structures appear without any visual explanation.

This situation requires the expertise of a radiologist to perform the cognitive task of reconstructing the 3D environment around the nodule 102 by scrolling through the image data in a 2D thick coronal projection mode, to intellectually relate information with that of the initial 2D thick axial projection image.

Figure 14:
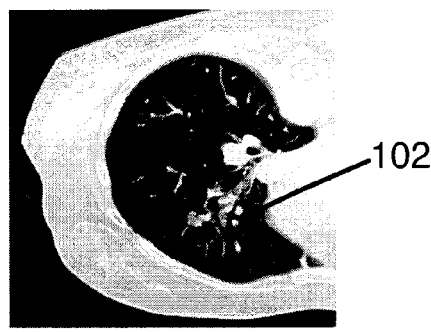
FIG. 14 is a screenshot which shows an initial 2D thick axial projection image.

Referring to FIG. 14, there is shown an initial 2D thick axial projection image equivalent to that of prior art shown FIG. 11.

In this embodiment, a user may provide an input on the nodule 102.

In fact, the input provided by the user may be indicative of a desire to zoom on a given portion of the image data (a region of interest for the operator to examine a structure of interest), in this case a portion of the image data comprising the nodule 102.

It will be appreciated by the skilled addressee that the input provided by the user may be of various types. In fact and in one embodiment, the input may comprise at least one of an interaction with a mouse and a keyboard.

Alternatively, the interaction may be performed via other input/output devices. In yet a further embodiment, the interaction may be performed via a combination of input/output devices with interactive graphical user elements resulting from the user input location in image data, current projection state and the like.

In one embodiment, the input provided by the user comprises a double-click performed using a mouse at a given location in the image displayed where the zoom has to be performed. In this particular case, the given location in the image is the location where the nodule 102 is displayed.

In a further embodiment, the input provided by the user may be indicative of a structure, e.g., a nodule, thus providing information for real-time segmentation of such structure to dynamically define a relevant region of interest allowing for the dynamic determination of a zoom ratio on that particular region of interest for the user to visually examine the specified structure designed by the input.

In another embodiment, the zoom is a default region of interest size around the input provided by the user.

Following the input provided by the user, and as shown further below, a transition comprising a sequence of a plurality of views will start from the initial 2D thick axial projection imaging and stop at a given zoomed ratio around a portion of the image data centered at the given location in the image.

Figure 18:
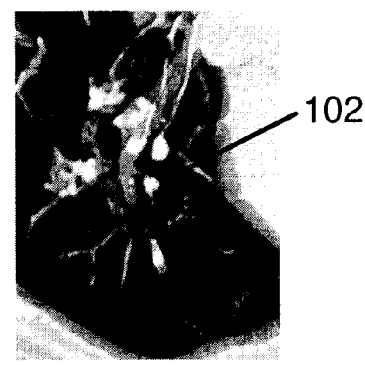
FIG. 18 is a screenshot which shows a desired final 2D thick axial projection image of a portion of the image data zoomed.

The start of the transition is illustrated at FIG. 14 while the stop or end of the transition is illustrated at FIG. 18. It will be appreciated that at least one of the plurality of views may comprise visual information displayed which is associated to at least one of an associated rendered projection and the input from the user.

Figure 15:
FIG. 15 is a screenshot which shows a view of a sequence of a plurality of views that comes chronologically after the view illustrated in FIG. 14.

FIG. 15 illustrates a view of the sequence of a plurality of views that is displayed to the user chronologically after the view illustrated at FIG. 14.

It will be appreciated by the skilled addressee that, although subtle, the rendered projection is different from the previous rendered projection as the projection view involves a 3D volume rendering, in traditional perspective ray casting, but with a field of view narrowed to 5 degrees, so that rays are almost parallel thus faking a 2D rendered projection view of a portion of the image data.

Figure 16:
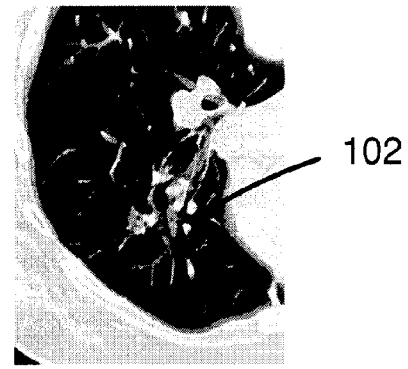
FIG. 16 is a screenshot which shows a view of a sequence of a plurality of views that comes chronologically after the view illustrated in FIG. 15.

FIG. 16 illustrates another view of the sequence of a plurality of views that is displayed to the user chronologically after the view illustrated at FIG. 15.

It will again be appreciated that, although subtle, the rendered projection is different from the previous rendered projection as the projection view involves a 3D volume rendering, in traditional perspective ray casting, but with a field of view narrowed to 5 degrees, so that rays are almost parallel thus faking a 2D rendered projection view of a portion of the image data.

Figure 17:
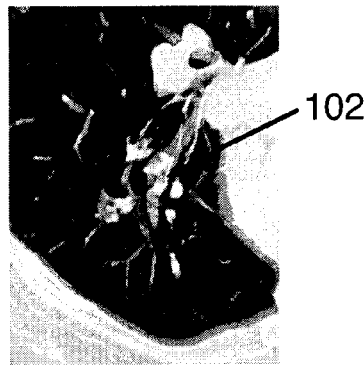
FIG. 17 is a screenshot which shows a view of a sequence of a plurality of views that comes chronologically after the view illustrated in FIG. 16.

FIG. 17 illustrates another view of the sequence of a plurality of views that is displayed to the user chronologically after the view illustrated at FIG. 16.

Now referring to FIG. 18, there is shown a desired final 2D thick axial projection of a portion of the image data zoomed and centered at the given location in the image.

Figure 19:
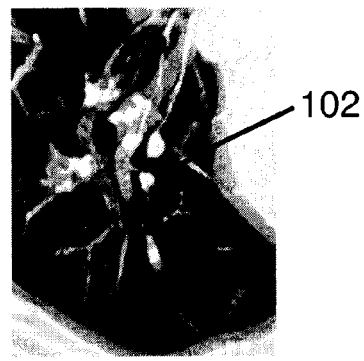
FIG. 19 is a screenshot which an initial 2D thick axial projection image zoomed.

Although the view shown in FIG. 19 is similar to the one shown in FIG. 18, it is now considered the initial 2D thick axial projection image zoomed.

In fact, it will be appreciated that an input may be then further provided by the user on the nodule 102 shown in FIG. 19, or elsewhere.

In fact, it will be appreciated that the input provided by the user may be of various types. In one embodiment, the input may comprise at least one of an interaction with a mouse and a keyboard.

Alternatively, the interaction may be performed via other input/output devices. In yet a further embodiment, the interaction may be performed via a combination of input/ output devices with interactive graphical user elements resulting from the user input location in image data, current projection state and the like.

In one embodiment, the input provided by the user comprises a click performed using a mouse at a given location in the image displayed. In this particular case, the given location in the image is where the nodule 102 is displayed.

It will be appreciated that in this case the input provided by the user may be indicative of a desire to modify the anatomical orientation of the rendered projection from an axial rendered projection to a coronal rendered projection on the portion of the image data.

Following the input provided by the user, and as shown further below, a transition comprising a sequence of a plurality of views will start from the initial 2D thick axial rendered projection image zoomed and stop with a 2D thick coronal rendered projection image of the portion of image data centered at the given location.

Figure 26:
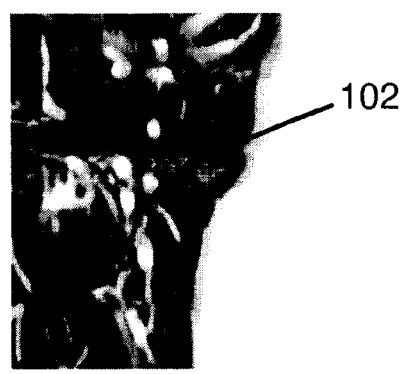
FIG. 26 is a screenshot which shows a desired final 2D thick coronal projection image equivalent to the view shown in FIG. 13.

It will be appreciated that the start of the transition is illustrated at FIG. 19 while the stop, or end, of the transition is illustrated at FIG. 26.

Figure 20:
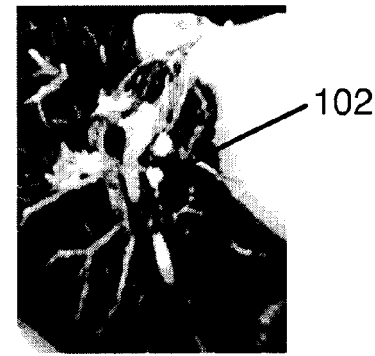
FIG. 20 is a screenshot which shows a view of a sequence of a plurality of views that comes chronologically after the view illustrated in FIG. 19.

FIG. 20 shows one of the views of the sequence of a plurality of views that comes chronologically after the previous view illustrated at FIG. 19.

It will be appreciated that the current rendered projection is different than the previous rendered projection illustrated at FIG. 19.

It will be further appreciated by the skilled addressee that the user is able to continuously visualize the nodule 102 and its surrounding environment through this current rendered projection and at different intermediary anatomical orientations. It will be further appreciated by the skilled addressee that the rendering of intermediary anatomical orientations derives from at least part of image data, as opposed to some prior-art methods where computer-generated information is unrelated to image data and designed for the sole purpose of visual image continuity (introducing the user with information unrelated to image data).

As a consequence, the skilled addressee will appreciate that the user does not need any substantial cognitive effort to interpret the information presented due to the sequential continuity of visual information. As a consequence, the nodule 102 and its surrounding environment are readily distinguishable.

Figure 21:
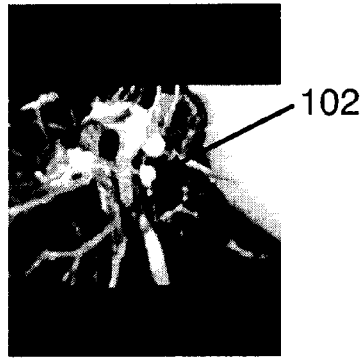
FIG. 21 is a screenshot which shows a view of a sequence of a plurality of views that comes chronologically after the view illustrated in FIG. 20.

FIG. 21 shows a view of the sequence of a plurality of views that is displayed to the user chronologically after the view shown in FIG. 20.

Figure 22:
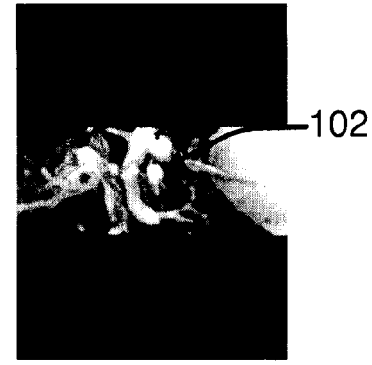
FIG. 22 is a screenshot which shows a view of a sequence of a plurality of views that comes chronologically after the view illustrated in FIG. 21.

FIG. 22 shows a view of the sequence of a plurality of views that is displayed to the user chronologically after the view shown in FIG. 21.

Figure 23:
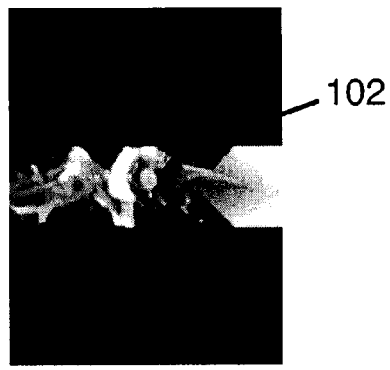
FIG. 23 is a screenshot which shows a view of a sequence of a plurality of views that comes chronologically after the view illustrated in FIG. 22.

FIG. 23 shows a view of the sequence of a plurality of views that is displayed to the user chronologically after the view shown in FIG. 22.

Figure 24:
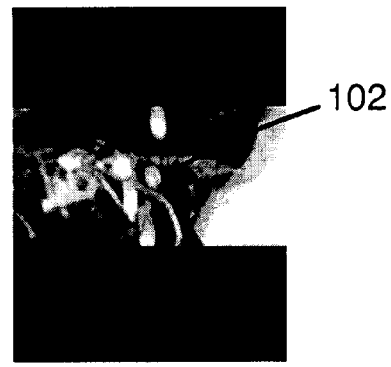
FIG. 24 is a screenshot which shows a view of a sequence of a plurality of views that comes chronologically after the view illustrated in FIG. 23.

FIG. 24 shows a view of the sequence of a plurality of views that is displayed to the user chronologically after the view shown in FIG. 23.

Figure 25:
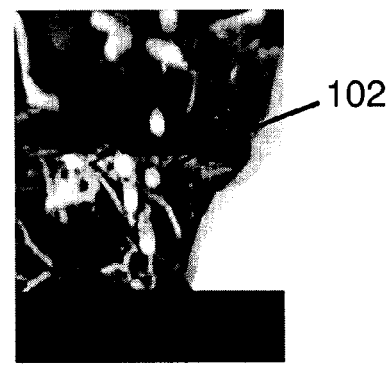
FIG. 25 is a screenshot which shows a view of a sequence of a plurality of views that comes chronologically after the view illustrated in FIG. 24.

FIG. 25 shows a view of the sequence of a plurality of views that is displayed to the user chronologically after the view shown in FIG. 24.

FIG. 26 shows a view which illustrates a desired final 2D thick coronal rendered projection image equivalent to that of prior art shown in FIG. 13.

It will be appreciated that by preventing the display of a "visual surprise" due to a sudden rendering of a different anatomical orientation of rendered projection image, the user can readily assess the nature of a specific element of a portion of the image data, which is of great advantage.

More precisely, and in the case illustrated herein, the radiologist will be able to readily determine from the sequence of a plurality of views displayed that a specific element of a portion of the image data has a round shape and therefore infer the presence of a nodule since no anatomical orientation does elongate.

Such determination would not have been possible using the prior art disclosed in FIG. 12 and FIG. 13.

Figure 27:
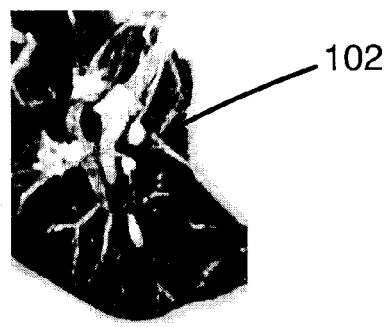
FIG. 27 is a screenshot which shows an initial 2D thick axial projection image.

Now referring to FIG. 27, there is shown a view similar to the view shown in FIG. 18. More precisely, this view is an initial 2D thick axial projection image.

In this embodiment, a user may provide an input on the nodule 102.

In fact, the input provided by the user may be indicative of a desire to modify the rendered projection from an initial axial rendered projection to a 3D volume rendering projection on a portion of the image data.

It will be appreciated by the skilled addressee that the input provided by the user may be of various types. In fact and in one embodiment, the input may comprise at least one of an interaction with a mouse and a keyboard.

Alternatively, the interaction may be performed via other input/output devices. In yet a further embodiment, the interaction may be performed via a combination of input/output devices with interactive graphical user elements resulting from the user input location in image data, current projection state and the like.

In one embodiment, the input provided by the user comprises a click-and-drag performed using a mouse at a given location in the image displayed. In this particular case, the given location in the image may be where the nodule 102 is displayed.

In this embodiment, the input provided by the user on the nodule 102 may be an indication of a desire to modify the rendered projection of the initial rendered projection from an axial rendered projection to a 3D volume rendering projection on the portion of the image data.

In yet another embodiment, in addition to indicating the location of a user's region of interest, the user input may enable the interactive determination of image data elements featuring similar image data characteristics than that of the input location neighborhood (e.g., interactive segmentation as mentioned previously). In such case, the input from the user comprises information associated with a segmentation to perform and the displaying in sequence of a plurality of views in the given window comprises performing a segmentation prior to displaying at least one of the plurality of views.

In a further embodiment, in addition to indicating the location of a user's region of interest, the input from the user may comprise location property data indicative of a structure's property as depicted by the elements of the image data, e.g., voxel intensity. The location property data may be used for determining rendering parameters (for real-time 3D transfer functions determination) associated with rendered projection for subsequent views (see IEEE Transaction on Visualization and Computer Graphics, vol. 8(3), July 2002, pp. 270-285, Multidimensional Transfer Functions for Interactive Volume Rendering) involved in 3D rendering. The location property data is used for determining rendering parameters associated with rendered projection for subsequent views.

This will be then followed by beginning a transition of sequence of a plurality of views that will start with the initial 2D thick axial projection image zoomed, and end with a 3D volume rendering projection image of the portion of image data centered at the given location.

It will be appreciated that the start of the transition is illustrated at FIG. 27 while the stop, or end, of the transition is illustrated at FIG. 33.

Figure 28:
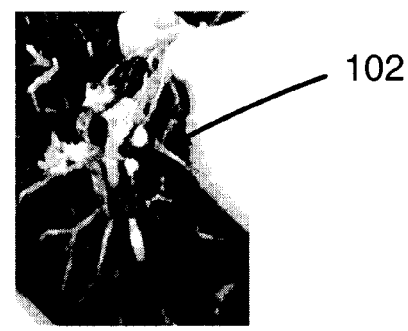
FIG. 28 is a screenshot which shows a view of the sequence of a plurality of views that comes chronologically after the view shown in FIG. 27.

FIG. 28 illustrates a view of the sequence of a plurality of views that is displayed to the user chronologically after the view shown in FIG. 27.

It will be appreciated by the skilled addressee that the current rendered projection is different from the previous rendered projection illustrated in FIG. 27.

It will be appreciated by the skilled addressee that the user is able to continuously visualize the nodule 102 and its environment through this current rendered projection and at different intermediary anatomical orientations.

The skilled addressee will further appreciate that the user does not need any substantial cognitive effort to interpret the information displayed due to the sequential continuity of visual information. The nodule 102 and its surrounding environment are readily distinguishable.

Now referring to FIG. 29, there is shown a view of a sequence of a plurality of views that is displayed to a user chronologically after the view shown in FIG. 28.

Specifically, this view combines a rendered projection similar, but not equivalent, to the previous view of FIG. 28, with a 3D volume rendering projection image view of the environment of the portion of the image data around the given location.

The skilled addressee will appreciate that, through this current rendered projection, the user is able to continuously visualize the nodule 102 and its environment and to further visually correlate 2D information with the arising 3D structure.

Now referring to FIG. 30, there is illustrated a view of the sequence of a plurality of views that is displayed chronologically after the view illustrated at FIG. 29.

Specifically, this view combines a rendered projection similar, but not equivalent, to the previous view illustrated in FIG. 29, with a 3D volume rendering projection image view of the environment of the portion of the image data around the given location.

It will be appreciated by the skilled addressee that, compared to FIG. 29, the combination of a rendered projection similar to the one of the previous view illustrated in FIG. 29 with a 3D volume rendering projection enhances the 3D volume rendering projection image compared to the previous view so as to get continuously closer to the user desired final 3D volume rendering projection image.

Now referring to FIG. 33, there is shown the desired final 3D volume rendering projection image.

It will be appreciated by the skilled addressee that it is possible for the user to readily assess the nature of the element of the portion of the image data by preventing the display of a "visual surprise" due to a sudden arising of a complex 3D structure in the environment of the nodule 102.

More precisely, as a radiologist will be able to readily determine from the sequence of a plurality of views that a specific element of the portion of the image data has a round shape and therefore infer the presence of a nodule thanks to the nature of the information provided in a 3D environment.

Although the view shown in FIG. 34 is similar to the one illustrated at FIG. 33, it is now considered as an initial 3D rendered projection image.

In fact, it will be appreciated that an input may be provided by the user.

The skilled addressee will appreciate that the input provided by the user may be of various types. In fact and in one embodiment, the input may comprise at least one of an interaction with a mouse and a keyboard.

Alternatively, the interaction may be performed via other input/output devices. In yet a further embodiment, the interaction may be performed via a combination of input/output devices with interactive graphical user elements resulting from the user input location in image data, current projection state and the like.

In fact, it will be appreciated that in this case, the input provided by the user may be indicative of a desire to spatially determine the location of a current portion of the image data with respect to a 2D thick coronal rendered projection of the image data.

Specifically, for a radiologist, this provides anatomical and spatial correlation to the Hilum of lung often used to correlate a region of interest between different lung exams during patient follow-ups to validate that one region under investigation corresponds to another region in a separate image data, generated by a 3D scanner device at a different time.

Following the input provided by the user, and as further shown below, a transition of a sequence of a plurality of views will start from the initial 3D volume rendering projection image and stop at a 3D volume rendering projection image of the portion of image data combined with a 2D thick coronal rendered projection of the image data.

The start of the transition is illustrated at FIG. 34 while the end or stop of the transition is illustrated at FIG. 38.

Now referring to FIG. 35, there is illustrated a view of the sequence of a plurality of views that is displayed chronologically after the view shown in FIG. 34.

The skilled addressee will appreciate that the current rendered projection is different from the previous rendered projection of FIG. 34, for both the 3D volume rendering projection image and the 2D thick rendered projection.

Through this current rendered projection, the user may continuously visualize a portion of the image data and its environment, and at different intermediary anatomical orientation.

It will be appreciated that the user does not need any substantial cognitive effort to interpret the information displayed due to the sequential continuity of visual information.

Now referring to FIG. 36, there is illustrated a view of the sequence of a plurality of views that is displayed chronologically after the view shown in FIG. 35.

It will be appreciated by the skilled addressee that the current rendered projection is different from the previous rendered projection of FIG. 35, for both the 3D volume rendering projection image and the 2D thick rendered projection.

Through this current rendered projection, the user may continuously visualize the portion of the image data and its environment, and at different intermediary anatomical orientation.

Again, it will be appreciated that the user does not need any substantial cognitive effort to interpret the information displayed due to the sequential continuity of visual information.

Now referring to FIG. 37, there is illustrated a view of the sequence of a plurality of views that is displayed chronologically after the view shown in FIG. 36.

The skilled addressee will again appreciate that the current rendered projection is different from the previous rendered projection shown at FIG. 36, for both the 3D volume rendering projection image and the 2D thick rendered projection.

It will be appreciated that, through this current rendered projection, the user may continuously visualize the portion of the image data and its environment, and at different intermediary anatomical orientation.

Now referring to FIG. 38, there is illustrated the final rendered projection image of the portion of the image data with respect to a 2D thick coronal rendered projection image of the image data.

It will be appreciated by the skilled addressee that by preventing the display of a "visual surprise" due to sudden arising of the entire image data, the user can readily assess the location of the portion of the image data.

Figure 31:
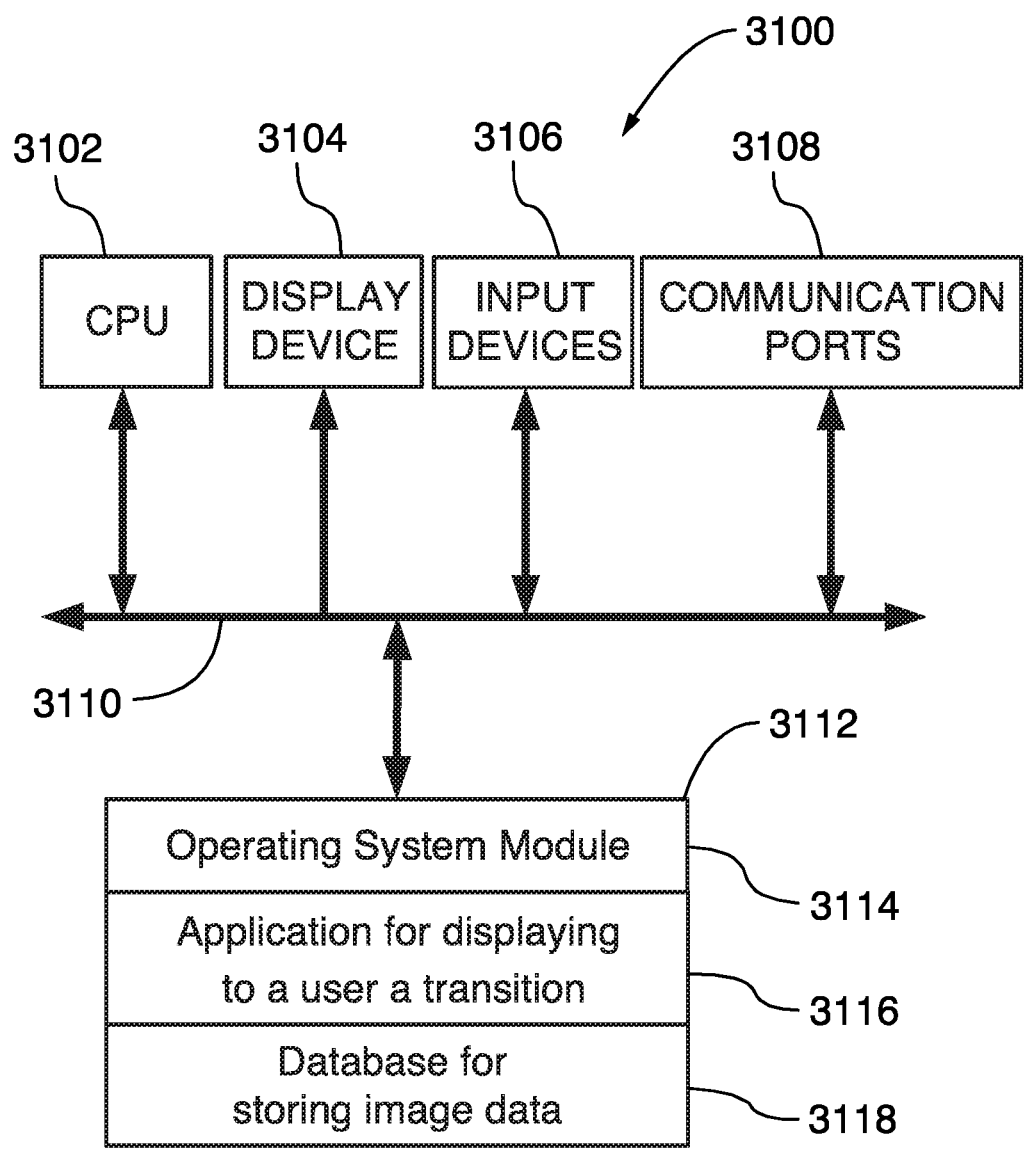
FIG. 31 is a block diagram which shows an embodiment of a system for displaying to a user a transition between a first rendered projection of a first image data and a final rendered projection of a second image data providing a method for displaying image data.

Now referring to FIG. 31, there is shown an embodiment of a system for displaying to a user a transition between a first rendered projection of a first image data and a final rendered projection of a second image data.

In this embodiment, the system for displaying to a user a transition between a first rendered projection of a first image data and a final rendered projection of a second image data 3100 comprises a central processing unit (CPU) 3102, a display device 3104, input devices 3106, communication ports 3108, a data bus 3110, and a memory 3112.

The central processing unit (CPU) 3102, the display device 3104, the input devices 3106, the communication ports 3108 and the memory 3112 are operatively interconnected via the data bus 3110.

The display device 3104 is used for displaying data to a user.

It will be appreciated by the skilled addressee that the display device 3104 may be of various types.

In one embodiment, the display device 3104 is a standard liquid-crystal display (LCD).

The input devices 3106 are used for enabling a user to provide an input. The input may be of various types depending on the input devices.

In one embodiment, the input devices 3106 comprise a keyboard and a mouse.

The skilled addressee will appreciate that various embodiments may be possible for the input devices 3106.

For instance, it will be appreciated that in one embodiment, the input device 3106 may be integrated with a display device 3104 to form a touchscreen display, such that the user will provide at least one part of its input using finger gestures performed on the screen of the display device 3104.

The communication ports 3108 are used for sharing data between the system for displaying to a user a transition between a first rendered projection of a first image data and a final rendered projection of a second image data 3100 and a remote processing unit.

More precisely, it will be appreciated that the communication ports 3108 are used for communicating with a 3D scanning device.

More precisely, the communication ports 3108 may comprise a first communication port operatively connected to a first 3D scanning device. The communication port 3108 may comprise a second communication port operatively connected to a second 3D scanning device.

It will be appreciated that the connection to the first and the second 3D scanning device may be performed via a data network.

The data network may comprise at least one of a local area network (LAN), a metropolitan area network (MAN) and a wide area network (WAN).

In one embodiment, the data network comprises the Internet.

It will be appreciated that the central processing unit (CPU) 3102 may be of various types.

In fact, it will be appreciated by the skilled addressee that the specifications of the system for displaying image data 3100 may vary greatly from the most basic computer to an advanced server.

The memory 3112 is used for storing data.

The skilled addressee will appreciate that the memory 3112 may be of various types.

More precisely and in one embodiment, the memory 3112 comprises an operating system module 3114, an application for displaying to a user a transition between a first rendered projection of a first image data and a final rendered projection of a second image data 3116 and a database for storing image data 3118.

In one embodiment, the operating system module 3114 is provided by Microsoft™.

Alternatively, the operating system module 3114 is selected from a group consisting is OS X manufactured by Apple™, Linux, etc.

Still in one embodiment, the application for displaying to a user a transition between a first rendered projection of a first image data and a final rendered projection of a second image data 3116 comprises instructions for obtaining the first image data and the second image data, each generated by a corresponding 3D scanning device scanning the same structure. It will be appreciated that in one embodiment, the scanning acquisition happens at the same time by corresponding 3D scanning device, e.g., using PET/CT technologies. It will be further appreciated that in another embodiment, the scanning acquisition happens at different time by corresponding 3D scanned device, e.g., CT scan follow-ups for the evaluation of lung patient response to therapy. It will be appreciated that in one embodiment the first image data and the second image data are obtained directly from a corresponding 3D scanning device via the communication ports 3108. In an alternative embodiment the first image data and the second image data are obtained from the memory 3118.

The application for displaying to a user a transition between a first rendered projection of a first image data and a final rendered projection of a second image data 3116 further comprises instructions for displaying a first view corresponding to a first rendered projection of the first image data in a given window. It will be appreciated that the first view is displayed in a given window of the display device 3104.

The application for displaying to a user a transition between a first rendered projection of a first image data and a final rendered projection of a second image data 3116 further comprises instructions for obtaining an input from the user, the input being indicative of the final rendered projection of a portion of the second image data. It will be appreciated that in one embodiment the input from the user provides information for the determination of required spatial transformation allowing for morphologically fitting the first and second image data prior rendering (e.g., using methods detailed in Journal of Applied Clinical Medical Physics, Vol. 14, No. 1, 2013; Registration of PET and CT images based on multiresolution gradient of mutual information demons algorithm for positioning esophageal cancer patients).

The application for displaying to a user a transition between a first rendered projection of a first image data and a final rendered projection of a second image data 3116 further comprises instructions for displaying in sequence a plurality of views in the given window of the display device, each view corresponding to a different rendered projection of at least one of the first image data and the second image data.

The plurality of rendered projections are defined so as to perform a transition between the first rendered projection and the final rendered projection.

The transition enables a sequential display of a continuity of information of the structure from the first image data to the portion of the second image data. It will be appreciated that at least the first rendered projection and the final rendered projection are defined according to a different spatial arrangement. It will be appreciated that in one embodiment the first image data and the second image data are generated by different 3D scanning devices. It will be further appreciated that in another embodiment, the first image data and the second image data are generated by a similar 3D scanning devices but at different points in time.

The database for storing image data 3118 further comprises the first image data and the second image data.

It will be appreciated that the image data may be stored according to various embodiments as known by the skilled addressee.

Also, it will be appreciated that a non-transitory computer-readable storage medium may be provided for storing computer-executable instructions. Such computer-executable instructions, when executed, would cause a computing device to perform a method for displaying to a user a transition between a first rendered projection of a first image data and a final rendered projection of a second image data, the method comprising obtaining the first image data and the second image data, each generated by a corresponding 3D scanning device scanning a structure; displaying a first view corresponding to a first rendered projection of the first image data in a given window; obtaining an input from the user, the input being indicative of the final rendered projection of a portion of the second image data; displaying in sequence a plurality of views in the given window, each view corresponding to a different rendered projection of at least one of the first image data and the second image data, wherein the plurality of rendered projections are defined so as to perform a transition between the first rendered projection and the final rendered projection, further wherein the transition enables a sequential display of a continuity of information of the structure from the first image data to the portion of the second image data, further wherein at least one of the first rendered projection and the final rendered projection are defined according to a different spatial arrangement and the first image data and the second image data are generated by different 3D scanning devices.

Figure 32:
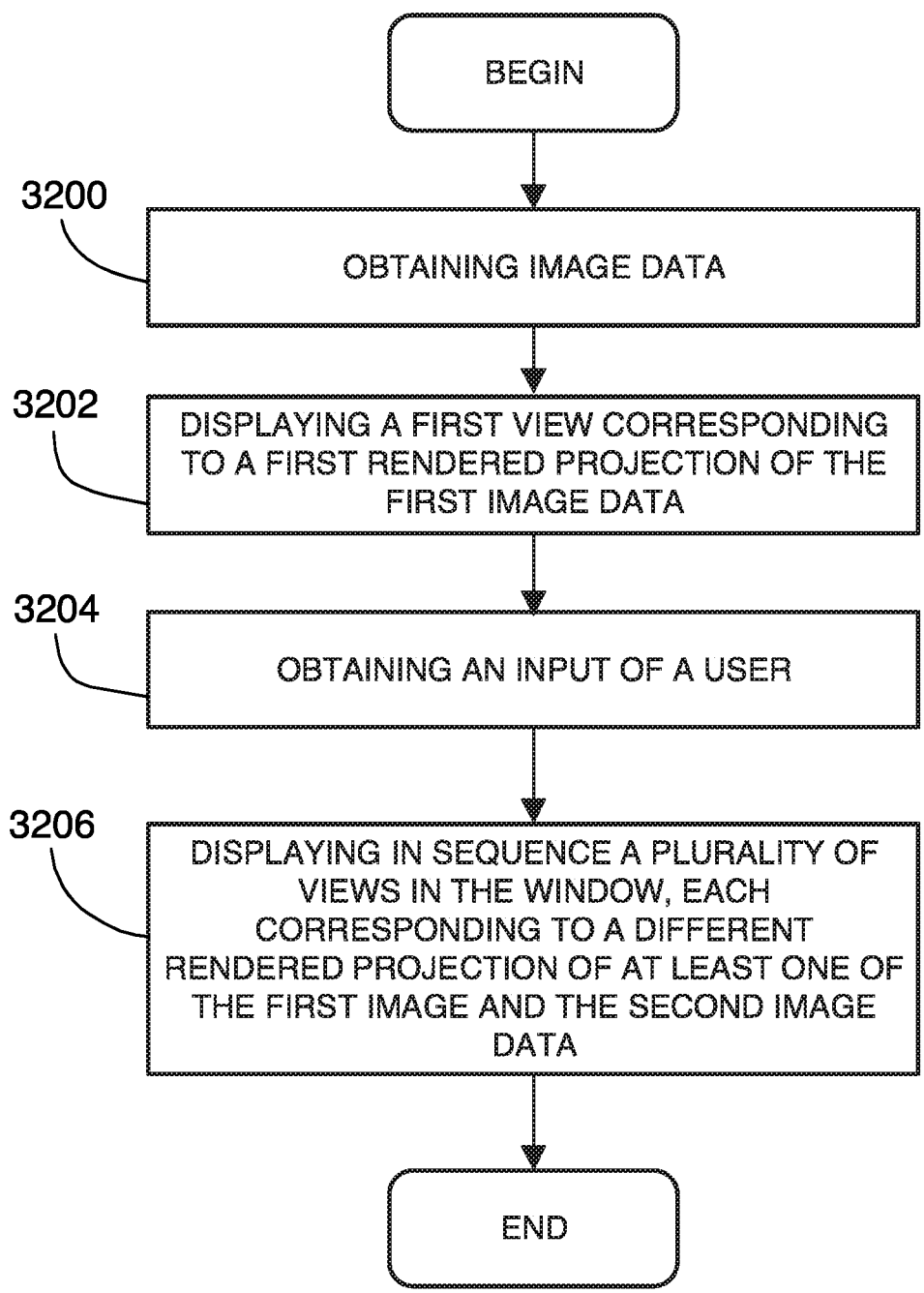
FIG. 32 is a flowchart which shows a first embodiment of a method for displaying to a user a transition between a first rendered projection of a first image data and a final rendered projection of a second image data providing a method for displaying image data.

Now referring to FIG. 32, there is shown an embodiment of a method for displaying to a user a transition between a first rendered projection of a first image data and a final rendered projection of a second image data.

According to processing step 3200, image data is obtained. It will be appreciated that the obtaining of the image data comprises obtaining a first image data and a second image data.

In one embodiment, each of the first image data and the second image data is generated by a corresponding 3D scanning device scanning a structure.

In an alternative embodiment, the first image data and the second image data is generated by a single 3D scanning device scanning a structure.

In another embodiment, it will be appreciated that the 3D scanning device is selected from a group consisting of at least one of a computerized tomography (CT) scan device, a tomosynthesis device, a magnetic resonance imaging (MRI) device, a positron emission tomography (PET) device and an ultrasound device.

In an alternative embodiment, the obtaining of said first image data and said second image data comprises retrieving said first image data and said second image data from a database for storing image data.

It will be appreciated that a structure may be a tangible or an intangible entity that can itself be an object, such as a biological structure (an organ) or physical structure (e.g., material element), or an attribute of such object, such as a functional representation of a given organ activity or functional behavior of a material element under certain constraints.

By means of nonrestrictive example, a structure can be either of a brain or a representation of brain activity, and a rod or a representation of a rod's elasticity.

By means of further nonrestrictive illustration of the previous example, a structure, such as a brain, may be scanned in 3D using a magnetic resonance imaging (MM) device, whereas a brain's activity may be scanned in 3D using a positron emission tomography (PET) device.

According to processing step 3202, a first view corresponding to a first rendered projection of the first image data is displayed in a given window.

It will be appreciated that the first rendered projection of the first image data may be of various types as illustrated above.

In fact and in one embodiment, the first rendered projection of the first image data is selected from a group consisting of 2D thin slice, 2D thick slice, 2D maximum intensity projection, 3D ray-tracing, 3D surface rendering, 3D perspective projection, 3D endoscopic projection and world projection.

It will be appreciated that, in one embodiment, the given window is comprised in a graphical user interface (GUI) displayed on a display unit of the user.

Alternatively, the given window is a player for displaying image data.

According to processing step 3204, an input is obtained from the user. The input is indicative of the final rendered projection of a portion of the second image data.

It will be appreciated that the final rendered projection of the portion of the second image data may be of various types as illustrated above.

In fact and in one embodiment, the final rendered projection of the portion of the second image data is selected from a group consisting of 2D thin slice, 2D thick slice, 2D maximum intensity projection, 3D ray-tracing, 3D surface rendering, 3D perspective projection, 3D endoscopic projection and world projection.

It will be appreciated by the skilled addressee that the input may be provided by the user according to various embodiments.

In one embodiment, the input is provided using an interaction of the user with the given window. In fact, the input may be provided using at least one of a mouse and a keyboard.

In an alternative embodiment, the interaction may be detected via a medical device used during a procedure in the case of a medical application. In such embodiment, the medical device may be an endoscope coupled to an apparatus for displaying to a user a transition between a first rendered projection of a first image data and a final rendered projection of a second image data.

According to processing step 3206, a plurality of views is displayed in sequence in the given window.

It will be appreciated that in one embodiment, the displaying of the first view corresponding to a first rendered projection of the first image data in a given window is performed on a touchscreen display.

Each view of the plurality of views corresponds to different rendered projections of at least one of the first image data and the second image data.

The plurality of rendered projections is defined so as to perform a transition between the first rendered projection and the final rendered projection.

Moreover, the transition enables a sequential display of a continuity of information of the structure from the first image data to the portion of the second image data.

It will be appreciated that at least the first rendered projection and the final rendered projection are defined according to a different spatial arrangement and the first image data and the second image data are generated by different 3D scanning devices.

It will be appreciated that the sequential display of a continuity of information refers to a visual perception enabling the interpretation of the surrounding environment of a region of interest in image data by processing information that is contained in image data generated by at least one 3D scanning device of a structure.

The processing of information refers to sequential displays of different spatial arrangements of image data that uses motion to create a visual correlation between different spatial arrangements of image data of a structure through the sequential display of elements in a composition. By means of example without limiting the foregoing, this method portrays the act or process for spatial arrangements to change place or direction, orientation, and position through the visual illustration of starting and stopping points, blurring of action.

It will be appreciated that spatial arrangement refers to the notion of the spatial property in which an array of things is placed. Referring to an image data generated by a 3D scanning device, and by means of nonlimitative example, an array of things can be either of an array of voxels representing the relaxation time of protons within certain anatomic tissues excited (and recorded) by a given radio-frequency fields generated (and received) by a MRI scanning device to generate image data of a brain, and an array of voxels representing the amount of gamma rays emitted by a positron-emitting radionuclide (tracer) injected in a structure such as the brain, and captured by a PET scanning device that generates image data of tracer concentration within a brain.

By means of further example, without limiting the foregoing, the spatial arrangement of image data in a 2D axial plane is different than that a 2D coronal plane, as both correspond to different means to arrange spatially at least a portion of image data. Conversely, interactively rotating a 3D model representing a given image data does not alter its spatial arrangement, neither does scrolling through an image data in a consistent 2D axial plane reviewing mode.

Clause 1: A method for displaying to a user a transition between a first rendered projection of a first image data and a final rendered projection of a second image data, the method comprising:

obtaining said first image data and said second image data, each generated by a corresponding 3D scanning device scanning a structure;

displaying a first view corresponding to a first rendered projection of said first image data in a given window;

obtaining an input from the user, said input being indicative of said final rendered projection of a portion of said second image data;

displaying in sequence a plurality of views in the given window, each view corresponding to a different rendered projection of at least one of the first image data and the second image data, wherein the plurality of rendered projections are defined so as to perform a transition between the first rendered projection and the final rendered projection, further wherein the transition enables a sequential display of a continuity of information of said structure from said first image data to said portion of said second image data, further wherein at least at least one of said first rendered projection and said final rendered projection are defined according to a different spatial arrangement and said first image data and said second image data are generated by different 3D scanning devices.

Clause 2: The method as claimed in clause 1, wherein the 3D scanning device is selected from a group consisting of at least one of a computerized tomography (CT) scan device, a tomosynthesis device, a magnetic resonance imaging (MM) device, a positron emission tomography (PET) device and an ultrasound device.

Clause 3: The method as claimed in any one of clauses 1 and 2, wherein the first rendered projection of the first image data is selected from a group consisting of 2D thin slice, 2D thick slice, 2D maximum intensity projection, 3D ray-tracing, 3D surface rendering, 3D perspective projection, 3D endoscopic projection and world projection.

Clause 4: The method as claimed in any one of clauses 1 to 3, wherein the final rendered projection is selected from a group consisting of 2D thin slice, 2D thick slice, 2D maximum intensity projection, 3D ray-tracing, 3D surface rendering, 3D perspective projection, 3D endoscopic projection and world projection.

Clause 5: The method as claimed in any one of clauses 1 to 4, wherein said first image data is generated by a first 3D scanning device scanning the structure and said second image data is generated by a second 3D scanning device scanning the structure.

Clause 6: The method as claimed in any one of clauses 1 to 4, wherein said first image data and said second image data are generated by a single 3D scanning device scanning the structure.

Clause 7: The method as claimed in any one of clauses 1 to 6, wherein the obtaining of an input from the user comprises obtaining said input from at least one of a keyboard and a mouse.

Clause 8: The method as claimed in any one of clauses 1 to 6, wherein the displaying of the first view corresponding to a first rendered projection of said first image data in a given window is performed on a touchscreen display, further wherein the obtaining of an input from the user comprises detecting a finger gesture on said touchscreen display.

Clause 9: The method as claimed in clause 1, wherein the obtaining of said first image data and said second image data comprises receiving said first image data and said second image data from a 3D scanning device scanning the structure.

Clause 10: The method as claimed in any one of clauses 1 to 8, wherein the obtaining of said first image data and said second image data comprises retrieving from a memory said first image data and said second image data.

Clause 11: The method as claimed in any one of clauses 1 to 10, wherein the obtaining of an input from the user comprises obtaining an indication of said final rendered projection of a portion of said second image data and an indication of a zoom to perform on a region of interest in a given view, further comprising generating a plurality of zoomed views in the given view, further wherein the plurality of views in the given windows comprises the generated plurality of zoomed views.

Clause 12: A system for displaying to a user a transition between a first rendered projection of a first image data and a final rendered projection of a second image data, the system comprising:
  a display device for displaying data to a user;
  a central processing unit operatively connected to the display device;
  an input device operatively connected to the central processing unit, said input device for obtaining an input from the user;
  a memory operatively connected to the central processing unit and comprising a database for storing the first image data and the second image data and an application for displaying to a user a transition between a first rendered projection of a first image data and a final rendered projection of a second image data, the application comprising:
    instructions for obtaining from said database said first image data and said second image data, each generated by a corresponding 3D scanning device scanning a structure;
    instructions for displaying on said display device a first view corresponding to a first rendered projection of said first image data in a given window;
    instructions for obtaining from said input device an input from the user, said input being indicative of said final rendered projection of a portion of said second image data;
    instructions for displaying on said display device in sequence a plurality of views in the given window, each view corresponding to a different rendered projection of at least one of the first image data and the second image data, wherein the plurality of rendered projections are defined so as to perform a transition between the first rendered projection and the final rendered projection, further wherein the transition enables a sequential display of a continuity of information of said structure from said first image data to said portion of said second image data, further wherein at least one of said first rendered projection and said final rendered projection are defined according to a different spatial arrangement and said first image data and said second image data are generated by different 3D scanning devices.

Clause 13: The system as claimed in clause 12, further comprising a communication port operatively connected to the central processing unit, the connection port for operatively connecting the system to a remote 3D scanning device scanning the structure.

Clause 14: The system as claimed in clause 13, wherein the communication port is operatively connected to the remote 3D scanning device scanning the structure via a data network.

Clause 15: The system as claimed in clause 14, wherein the data network is selected from a group consisting of a local area network (LAN), a metropolitan area network (MAN) and a wide area network (WAN).

Clause 16: The system as claimed in clause 15, wherein the data network comprises the Internet.

Clause 17: The system as claimed in clause 12, wherein the display device is a touchscreen display, further wherein at least one part of said input of said user is obtained from said touchscreen display.

Clause 18: A non-transitory computer-readable storage medium for storing computer-executable instructions which when executed cause a computing device to perform a method for displaying to a user a transition between a first rendered projection of a first image data and a final rendered projection of a second image data, the method comprising:
  obtaining said first image data and said second image data, each generated by a corresponding 3D scanning device scanning a structure;
  displaying a first view corresponding to a first rendered projection of said first image data in a given window;
  obtaining an input from the user, said input being indicative of said final rendered projection of a portion of said second image data;
  displaying in sequence a plurality of views in the given window, each view corresponding to a different rendered projection of at least one of the first image data and the second image data, wherein the plurality of rendered projections are defined so as to perform a transition between the first rendered projection and the final rendered projection, further wherein the transition enables a sequential display of a continuity of information of said structure from said first image data to said portion of said second image data, further wherein at least one of said first rendered projection and said final rendered projection are defined according to a different spatial arrangement and said first image data and said second image data are generated by different 3D scanning devices.

Clause 19: The method as claimed in any one of clauses 1 to 11, wherein at least one of the plurality of views further comprises visual information displayed which is associated to at least one of an associated rendered projection and the input from the user.

Clause 20: The method as claimed in any one of clauses 1 to 11 and 19, wherein the input from the user further comprises location property data in said first image data, further wherein the location property data is used for determining rendering parameters associated with rendered projection for subsequent views.

Clause 21: The method as claimed in any one of clauses 1 to 11 and 19 to 20, wherein the input from the user comprises information associated with a segmentation to perform, further wherein the displaying in sequence of a plurality of views in the given window comprises performing a segmentation prior displaying at least one of the plurality of views.

Although the above description relates to a specific preferred embodiment as presently contemplated by the inventor, it will be understood that the invention in its broad aspect includes mechanical and functional equivalents of the elements described herein.

The invention claimed is:

1. A method for displaying to a user a transition between a first rendered projection of a first image data and a final rendered projection of a second image data, the method comprising:
  obtaining said first image data and said second image data, each generated by a corresponding 3D scanning device scanning a structure, wherein the structure is an anatomical structure that includes a region of interest;
  displaying a first view corresponding to a first rendered projection of said first image data in a given window, wherein said first rendered projection is generated by rendering at least part of said first image data at a given viewpoint;
  obtaining an input from the user, said input being indicative of said final rendered projection of a portion of said second image data, wherein the portion of said second image data includes the region of interest; and displaying in sequence a plurality of views in the given window, each view corresponding to a different rendered projection of a different intermediary direction, orientation, and/or position of said structure based on at least one of the first image data and the second image data, wherein the plurality of rendered projections are defined so as to perform a transition between the first rendered projection and the final rendered projection, wherein the transition enables a sequential display of a continuity of information from said first image data to said portion of said second image data, wherein at least said first rendered projection and said final rendered projection are defined according to a different spatial arrangement, wherein a given spatial arrangement refers to one of a given multiplanar reconstruction technique and a given volume rendering technique used to generate a view of a portion of a given image data, and wherein the transition corresponds to a visual perception enabling the interpretation of said region of interest and its surrounding environment in the scanned structure in said given window by using motion of the different spatial arrangements to create a visual correlation between the different spatial arrangements.

2. The method as claimed in claim 1, wherein the 3D scanning device is selected from a group consisting of at least one of a computerized tomography (CT) scan device, a tomosynthesis device, a magnetic resonance imaging (MRI) device, a positron emission tomography (PET) device, and an ultrasound device.

3. The method as claimed in claim 1, wherein the first rendered projection of the first image data is selected from a group consisting of 2D thin slice, 2D thick slice, 2D maximum intensity projection, 3D ray-tracing, 3D surface rendering, 3D perspective projection, 3D endoscopic projection, and world projection.

4. The method as claimed in claim 3, wherein the final rendered projection is selected from a group consisting of 2D thin slice, 2D thick slice, 2D maximum intensity projection, 3D ray-tracing, 3D surface rendering, 3D perspective projection, 3D endoscopic projection, and world projection.

5. The method as claimed in claim 4, wherein said first image data is generated by a first 3D scanning device scanning the structure and said second image data is generated by a second 3D scanning device scanning the structure.

6. The method as claimed in claim 4, wherein said first image data and said second image data are generated by a single 3D scanning device scanning the structure.

7. The method as claimed in claim 6, wherein the obtaining of an input from the user comprises obtaining said input from at least one of a keyboard and a mouse.

8. The method as claimed in claim 6, wherein the displaying of the first view corresponding to a first rendered projection of said first image data in a given window is performed on a touchscreen display, further wherein the obtaining of an input from the user comprises detecting a finger gesture on said touchscreen display.

9. The method as claimed in claim 8, wherein the obtaining of said first image data and said second image data comprises retrieving from a memory said first image data and said second image data.

10. The method as claimed in claim 9, wherein the obtaining of an input from the user comprises obtaining an indication of said final rendered projection of a portion of said second image data and an indication of a zoom to perform on a region of interest in a given view, further comprising generating a plurality of zoomed views in the given view, further wherein the plurality of views in the given window comprises the generated plurality of zoomed views.

11. The method as claimed in claim 10, wherein at least one of the plurality of views further comprises visual information displayed which is associated to at least one of an associated rendered projection and the input from the user.

12. The method as claimed in claim 1, wherein the obtaining of said first image data and said second image data comprises receiving said first image data and said second image data from a 3D scanning device scanning the structure.

13. A system for displaying to a user a transition between a first rendered projection of a first image data and a final rendered projection of a second image data, the system comprising:

a display device for displaying data to a user;

a central processing unit operatively connected to the display device;

an input device operatively connected to the central processing unit, said input device for obtaining an input from the user; and a memory operatively connected to the central processing unit and comprising a database for storing the first image data and the second image data and an application for displaying to a user a transition between a first rendered projection of a first image data and a final rendered projection of a second image data, wherein said first rendered projection is generated by rendering at least part of said first image data at a given viewpoint, the application comprising:

instructions for obtaining from said database said first image data and said second image data, each generated by a corresponding 3D scanning device scanning a structure, wherein the structure is an anatomical structure that includes a region of interest;

instructions for displaying on said display device a first view corresponding to a first rendered projection of said first image data in a given window;

instructions for obtaining from said input device an input from the user, said input being indicative of said final rendered projection of a portion of said second image data, wherein the portion of said second image data includes the region of interest; and instructions for displaying on said display device in sequence a plurality of views in the given window, each view corresponding to a different rendered projection of a different intermediary direction, orientation, and/or position of said structure based on at least one of the first image data and the second image data, wherein the plurality of rendered projections are defined so as to perform a transition between the first rendered projection and the final rendered projection, wherein the transition enables a sequential display of a continuity of information from said first image data to said portion of said second image data, wherein at least said first rendered projection and said final rendered projection are defined according to a different spatial arrangement, wherein a given spatial arrangement refers to one of a given multiplanar reconstruction technique and a given volume rendering technique used to generate a view of a portion of a given image data, and wherein the transition corresponds to a visual perception enabling the interpretation of said region of interest and its surrounding environment in the scanned structure in said given window by using motion of the different spatial arrangements to create a visual correlation between the different spatial arrangements.

14. The system as claimed in claim 13, further comprising a communication port operatively connected to the central processing unit, the communication port for operatively connecting the system to a remote 3D scanning device scanning the structure.

15. The system as claimed in claim 14, wherein the communication port is operatively connected to the remote 3D scanning device scanning the structure via a data network.

16. The system as claimed in claim 15, wherein the data network is selected from a group consisting of a local area network (LAN), a metropolitan area network (MAN) and a wide area network (WAN).

17. The system as claimed in claim 16, wherein the data network comprises the Internet.

18. The system as claimed in claim 13, wherein the display device is a touchscreen display, further wherein at least one part of said input of said user is obtained from said touchscreen display.

19. A non-transitory computer-readable storage medium for storing computer-executable instructions which when executed cause a computing device to perform a method for displaying to a user a transition between a first rendered projection of a first image data and a final rendered projection of a second image data, wherein said first rendered projection is generated by rendering at least part of said first image data at a given viewpoint, the method comprising:

obtaining said first image data and said second image data, each generated by a corresponding 3D scanning device scanning a structure, wherein the structure is an anatomical structure that includes a region of interest;

displaying a first view corresponding to a first rendered projection of said first image data in a given window;

obtaining an input from the user, said input being indicative of said final rendered projection of a portion of said second image data, wherein the portion of said second image data includes the region of interest; and displaying in sequence a plurality of views in the given window, each view corresponding to a different rendered projection of a different intermediary direction, orientation, and/or position of said structure based on at least one of the first image data and the second image data, wherein the plurality of rendered projections are defined so as to perform a transition between the first rendered projection and the final rendered projection, wherein the transition enables a sequential display of a continuity of information from said first image data to said portion of said second image data, wherein at least said first rendered projection and said final rendered projection are defined according to a different spatial arrangement, wherein a given spatial arrangement refers to one of a given multiplanar reconstruction technique and a given volume rendering-technique used to generate a view of a portion of a given image data, and wherein the transition corresponds to a visual perception enabling interpretation of said region of interest and its surrounding environment in the scanned structure in said given window by using motion of the different spatial arrangements to create a visual correlation between the different spatial arrangements.

20. The method as claimed in claim 11, wherein the input from the user further comprises location property data in said first image data, further wherein the location property data is used for determining rendering parameters associated with rendered projection for subsequent views.

21. The method as claimed in claim 20, wherein the input from the user comprises information associated with a segmentation to perform, further wherein the displaying in sequence of a plurality of views in the given window comprises performing a segmentation prior to displaying at least one of the plurality of views.

* * * * *